United States Patent [19]

Ruiz

[11] Patent Number: 4,846,814
[45] Date of Patent: Jul. 11, 1989

[54] NON-WHIP CATHETER

[75] Inventor: Oscar F. Ruiz, Coconut Grove, Fla.

[73] Assignee: Sherwood Medical Company, St. Louis, Mo.

[21] Appl. No.: 177,199

[22] Filed: Apr. 4, 1988

Related U.S. Application Data

[63] Continuation of Ser. No. 819,203, Jan. 16, 1986, Pat. No. 4,735,620.

[51] Int. Cl.⁴ ............................................ H61M 25/00
[52] U.S. Cl. .................................... 604/281; 604/264
[58] Field of Search ............................ 604/280–281, 604/264, 170, 8–10; 128/658, 785, 656

[56] References Cited

U.S. PATENT DOCUMENTS

| | | | |
|---|---|---|---|
| 2,492,384 | 12/1949 | Kaslow | 604/280 |
| 3,419,010 | 12/1968 | Williamson | 604/170 |
| 3,890,977 | 6/1975 | Wilson | 128/785 |
| 4,279,252 | 7/1981 | Martin | 128/658 |
| 4,282,876 | 8/1981 | Flynn | 128/658 |
| 4,385,635 | 5/1983 | Ruiz | 128/658 |
| 4,563,181 | 1/1986 | Wijayarathna et al. | 604/280 |
| 4,735,620 | 4/1988 | Ruiz | 604/281 |

FOREIGN PATENT DOCUMENTS

| | | | |
|---|---|---|---|
| 2353078 | 5/1974 | Fed. Rep. of Germany | 128/656 |
| 3309052 | 9/1984 | Fed. Rep. of Germany | 604/264 |

OTHER PUBLICATIONS

A-V Cannula Systems, Quinton Instruments, 8-1969.

Primary Examiner—C. F. Rosenbaum
Assistant Examiner—Kathleen A. Daley
Attorney, Agent, or Firm—Stanley N. Garber; Andrew J. Beck; Richard D. Allison

[57] ABSTRACT

The angiographic catheter includes a long generally flexible portion of a first material, an intermediate portion of the first material and a second material that is more flexible then the first material and a tip portion of the second material. The long body portion has a first exit opening having a stream trajectory directed toward the exit stream trajectory from the tip member exit for stream breakup and mixing at. A reaction exit is directed in the opposite direction of the first exit opening.

The generally long body portion with a curved end portion with a first end curve of generally circular shape about a center that is connected to the end of the long body with a compound curve connected to the end of the first end curve and having a member positioned generally parallel to the long body portion with the distance between parallel members generally less than to the radii of the generally circular shape.

The long body member is generally the long generally flexible portion which is composed entirely of the first material. Approximately first ninety degrees of the first end curve is generally the intermediate portion composed of the first and second material. The rest of the first end curve and the compound curve is composed of the second material. The reaction from the stream exiting the tip member exit is to move the parallel portion back into the first end curve without other movement because of reaction from the streams exiting exits.

3 Claims, 1 Drawing Sheet

U.S. Patent    Jul. 11, 1989    4,846,814
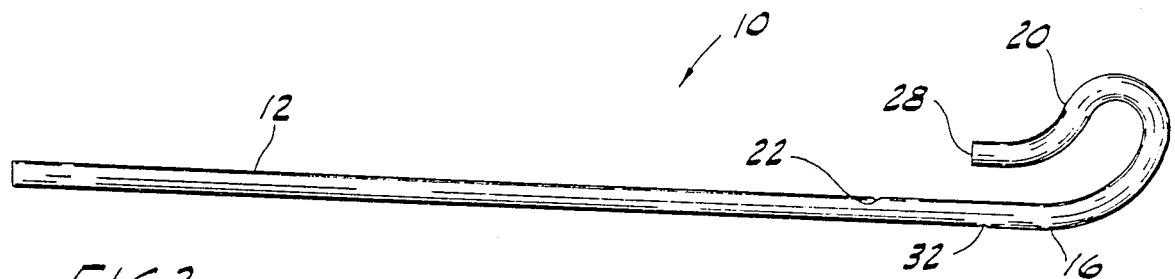
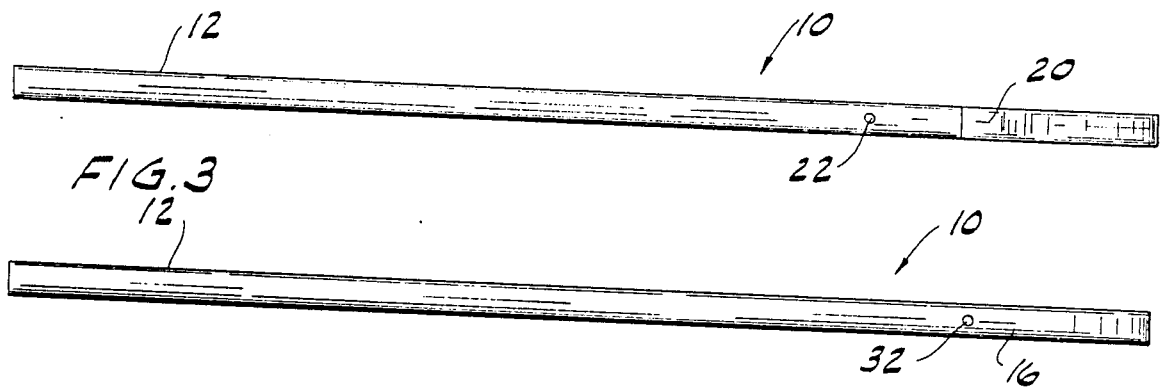
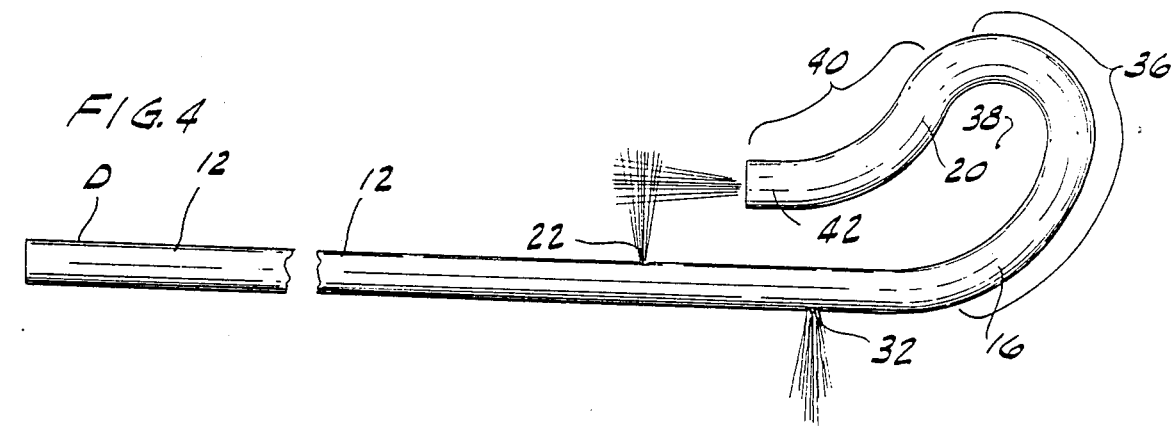
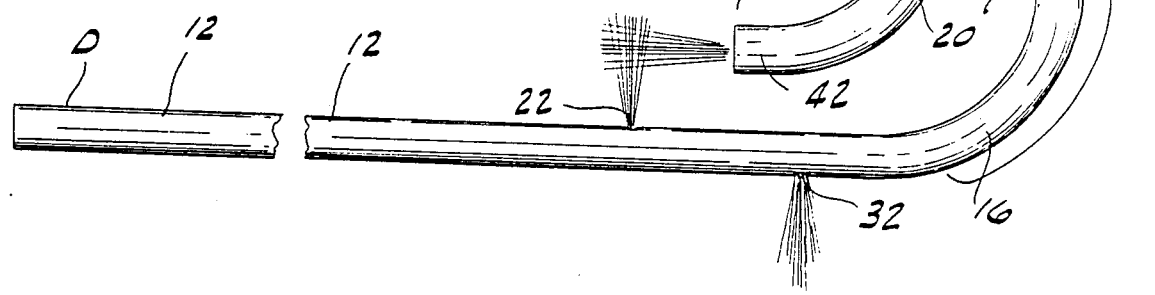
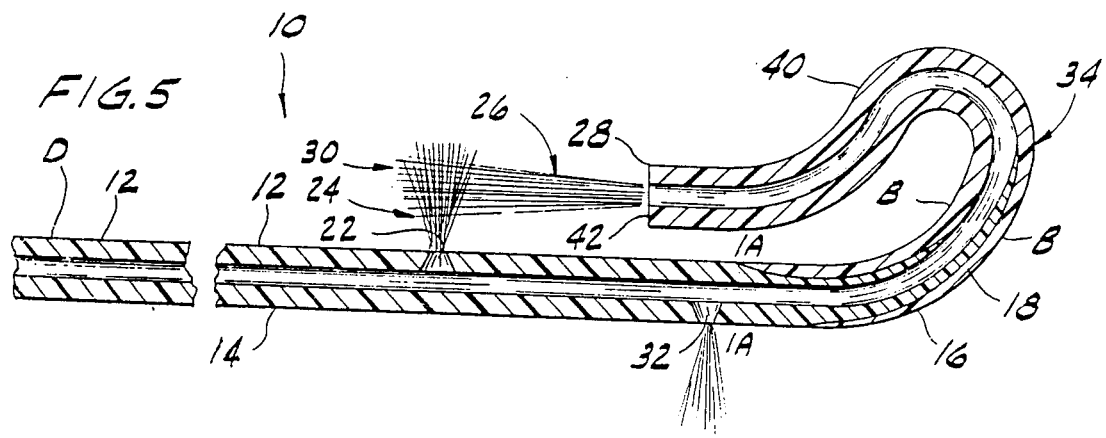

NON-WHIP CATHETER

This is a continuation of co-pending application Ser. No. 819,203 filed on Jan. 16, 1986 now U.S. Pat.No. 4,735,620.

BACKGROUND OF THE INVENTION

The present invention is to an angiographic catheter having three material portions and three shape portions and three exit opening to provide a non whip angiographic catheter.

In the past various shapes and designs have been proposed and used. All previous designs whip backward when high pressure fluid passes through the angiographic. Such movement can damage vessel walls. The high pressure fluid exiting the angiographic catheter if not controlled can damage vessel walls especially when the catheter whips back.

BRIEF DESCRIPTION OF THE INVENTION

The new and improved angiographic catheter invention includes a curved end having a main opening facing back in the longitudinal direction of the catheter body position. The catheter includes a long generally flexible portion of a first generally hard material, an intermediate portion of the first material and a second generally soft material and a tip portion of the second material. The long flexible body portion has a second exit opening having a stream trajectory directed toward the path of the main stream trajectory from the tip portion for stream breakup and mixing. A reaction exit facing in the opposite direction of the second exit opening.

The end of the long, flexible body portion is curved having generally circular shape about a center. The intermediate portion lies in the generally circular shape. A compound curve in the general shape of an S type shape is connected to the end of the circular shape. The long body portion, circular shape and compound curve lie in the same plane. The tip end is positioned generally parallel to the long body portion with the distance between parallel members generally less than to the radii of the generally circular shape.

The generally long flexible body portion is composed entirely of the first material that is harder and more rigid. Approximately first ninety degrees of the circular shaped end curve is generally the intermediate portion composed of the first and second materials. The first material decreases over the ninety degree and the second material increases over the ninety degrees. The rest of the circular shaped end curve and the compound curve is composed of the second softer material. The reaction from the stream exiting the main exit at the end of the tip portion moves the tip portion back into the circular shaped portion without other movement of the long flexible body portion because of the curves, materials and the other stream exits.

It is an object of this invention to provide a nonwhip angiographic catheter.

It is another object of this invention to provide an angiographic catheter that has a tip and that moves back in to the curved shape connecting the tip end to the main body portion.

It is a further object of this invention to provide a two material angiographic catheter to provide curved portion to absorb the main exit strean reaction.

BRIEF DESCRIPTION OF THE DRAWING

In the drawing:
FIG. 1 is a side view of the angiographic catheter.
FIG. 2 is a top view of FIG. 1.
FIG. 3 is a bottom view of FIG. 1.
FIG. 4 is an illustration with streams exiting the main exit and the second exit and the third exit.
FIG. 5 is a partial enlarged sectional view.

DESCRIPTION OF THE PREFERRED EMBODIMENT

Referring now to the drawings and the FIGS. 1 through 5, the angiographic catheter 10 includes a long generally flexible portion 12 of a first material 14, an intermediate portion 16 of the first material 14 and a second material 18 that is more flexible then the first material 14 and a tip portion 20 of the second material 18. The catheter has a main exit 28. The long body portion 12 has a first exit opening 22 having a stream trajectory 24, shown in FIG. 5, directed toward the exit stream trajectory 26 from the tip member exit 28. The streams intersect and breakup and mix as shown, at numeral 30. A reaction exit 32 is directed in the opposite direction of the first exit opening 22.

The generally long body portion 12 with a curved end portion 34 with a first end curve 36 of generally circular shape about a center 38 that is connected to the end of the long body with a compound curve 40 connected to the end of the first end curve 36 and having a member 42 positioned generally parallel to the long body portion 12 with the distance between parallel members 12 and 42 generally less than to the radii of the generally circular shape.

The long body member 12 is generally the long generally flexible portion which is composed entirely of the first material 18. Approximately first ninety degrees of the first end curve 36 is generally the intermediate portion composed of the first and second material. The rest of the first end curve 36 and the compound curve 40 is composed of the second material 18. The reaction from the stream exiting the tip member exit 28 is to move the parallel portion 42 back into the first end curve without other movement because of reaction from the streams exiting exits 22 and 32.

The material in portion 14 is preferrably a polyurethane. The material in portion 18 is preferrably a polyamide 18. The portion 36 includes in one embodiment a tapering portion of the polyurethane material from A to B. The portion A to B increases in thickness of the polyamide material 18. The catheter is used under high pressure.

The curved portion 36 may have a 0.5 mm radius. The portion solely of material 18 may be one inch long. The dual material portion from A to B may be one half inch long to three quarters of an inch long.

The catheter may be of one material or made of a plurality of material. The catheter may be of the shape disclosed with one material or of the plurality of materials in areas A to B and area 40 and 34 less A to B and area 14 in other shapes to provide the same results.

The instant invention has been shown and described herein in what is considered to be the most practical and prefered embodiment. It is recognized, however, that departures may be made therefrom within the scope of the invention and that obvious modifications will occur to a person skilled in the art.

What I claim is:

1. An angiographic catheter comprising:

a long generally flexible body portion of a first material;

a first end curve portion beginning at the end of said body portion;

said first end curve portion having a first intermediate portion of said first material and a second material and a curved end portion of said second material, said second material being more flexible than said first material;

said intermediate portion having a first and second end with said first end connected to said body portion;

said curved end portion having a first and second end with said first end connected to said second end of said intermediate portion;

a compound curve portion of said second material having a first and second end with said first end connected to said second end of said curved end portion and said second end comprising a tip portion having a first exit opening therein for the passage of a stream of liquid under pressure therethrough;

a second exit in said body portion positioned so that a stream of liquid under pressure exiting through the second exit intersects with the stream of liquid from the first exit opening in the tip portion to disperse the latter;

a third exit in said body portion positioned so that a stream of liquid under pressure exiting the third exit will oppose the pressure exerted by the stream of liquid exiting through the second exit while not intersecting the stream of liquid from the first exit.

2. An angiographic catheter comprising:

a long generally flexible body portion of a first material;

a first end curve portion beginning at the end of said body portion;

said first end curve portion having a first intermediate portion of said first material and a second material and a curved end portion of said second material, said second material being more flexible than said first material;

said intermediate portion having a first and second end with said first end connected to said body portion;

said curved end portion having a first and second end with said first end connected to said second end of said intermediate portion;

a compound curve portion of said second material having a first and second end with said first end connected to said second end of said curved end portion and said second end comprising a tip portion having a first exit opening for the passage of a stream of liquid under pressure therethrough;

a second exit in said body portion positioned so that a stream of liquid under pressure exiting through the second exit intersects the stream of liquid from the exit opening in the tip portion to disperse the latter;

a third exit opening in said body portion positioned so that a stream of liquid under pressure exiting the third exit will oppose the pressure from the streams of liquid exiting through the first and second exits; and said first, second and third exits are positioned so that the streams of liquid exiting the first, second and third exits are substantially coplaner.

3. An angiographic catheter comprising:

a long generally flexible body portion of a first material;

a first end curve portion beginning at the end of said body portion;

said first end curve portion having a first intermediate portion of said first material and a second material and a curved end portion of said second material, said second material being more flexible than said first material;

said intermediate portion having a first and second end with said first end connected to said body portion;

said curved end portion having a first and second end with said first end connected to said second end of said intermediate portion;

a compound curve portion having a first and second end wherein said first end is connected to said second end of said curved end;

said compound curve portion having a tip portion with an exit opening on said second end for the passage of a stream of liquid under pressure therethrough; and the curvature of said compound curve portion causing a curvature reaction from the stream of liquid exiting the exit opening in the tip portion to move said tip portion generally adjacent said first curve portion.

* * * * *